United States Patent [19]
Iacobelli et al.

[11] Patent Number: 6,030,963
[45] Date of Patent: Feb. 29, 2000

[54] 16-ENE-26,27-BISHOMO CHOLECALCIFEROLS

[75] Inventors: Jerome Anthony Iacobelli, Paramus; Milan Radoje Uskokovic, Upper Montclair, both of N.J.

[73] Assignee: Hoffmann-La Roche Inc., Nutley, N.J.

[21] Appl. No.: 09/127,449

[22] Filed: Jul. 31, 1998

Related U.S. Application Data

[63] Continuation of application No. 08/748,878, Nov. 14, 1996, abandoned.
[60] Provisional application No. 60/008,744, Nov. 22, 1995.

[51] Int. Cl.[7] .......................... A01N 45/00; C07C 401/00
[52] U.S. Cl. .............................................. 514/167; 552/653
[58] Field of Search ........................... 552/653; 514/167; 568/819

[56] References Cited

U.S. PATENT DOCUMENTS

| | | | |
|---|---|---|---|
| 5,087,619 | 2/1992 | Baggiolini et al. | 514/167 |
| 5,145,846 | 9/1992 | Baggiolini | 514/167 |
| 5,393,900 | 2/1995 | Doran et al. | 552/505 |

FOREIGN PATENT DOCUMENTS

| | | | |
|---|---|---|---|
| 0 325 279 | 6/1989 | European Pat. Off. | |
| 325279 A1 | 6/1989 | European Pat. Off. | C07C 172/00 |

OTHER PUBLICATIONS

Clark et al., Effects of analogs 1,25(OH)2D3 on Proliferation and Differentiation, J. Can Res. Clin. Oncol., 118(3), 190–4, 1992.

Chem. Abstr. vol. 114, No. 5, Feb. 4, 1991, p. 91, col. 1, A. W. Norman, et al. Abstract No. 36131.

Chem. Abstr. vol. 110, No. 9 Feb. 27, 1989 Abstr. No. 69512, E.D. Collins, et al. p. 67, col. 2.

Blood, vol. 78, No. 1, Jul. 1, 1991, pp. 75–82, Jian–Yuan Zhou, et al.

Cancer Letters, vol. 92, No. 1, May 25, 1995 pp. 77–82, Brenner, R.V., et al.

Steroids: Structure, Function & Regulation, vol. 56, No. 3, Mar. 1991 pp. 142–146, A. Honda, et al.

Blood, vol. 88, No. 6, Sep. 15, 1996 pp. 2201–2209, R. Munker, et al.

Mol. Endocrinol. vol. 9, No. 12, Dec. 1995 pp. 1814–1824, B. Cheskis, et al.

*Primary Examiner*—Jose' G. Dees
*Assistant Examiner*—Alton Pryor
*Attorney, Agent, or Firm*—George W. Johnston; Patricia S. Rocha-Tramaloni; Robert A. Silverman

[57] ABSTRACT

The invention relates to a compound of the formula

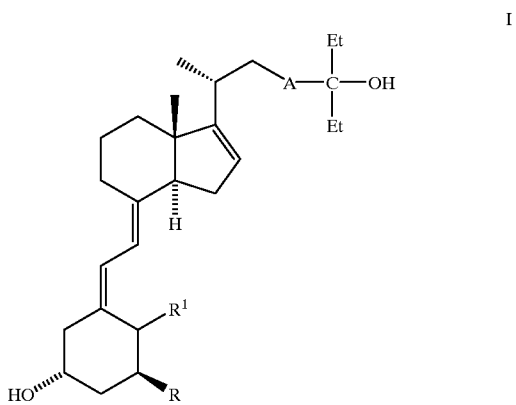

wherein A is

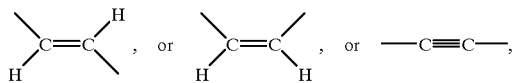

Et is ethyl, and R is hydroxy and $R^1$ is hydrogen or $=CH_2$ or R is hydrogen or fluoro and $R^1$ is $=CH_2$. Compounds of formula I stimulate HL-60 cell differentiation. Accordingly, the compounds of formula I are useful as agents for the treatment of neoplastic diseases, such as leukemia.

22 Claims, No Drawings

16-ENE-26,27-BISHOMO CHOLECALCIFEROLS

This is a continuation of Ser. No. 08/748,878, filed on Nov. 14, 1996 now abandoned. This application claims the benefit under 35 U.S.C. of the U.S. provisional application No. 60/008,774 filed Nov. 22, 1995.

BRIEF SUMMARY OF THE INVENTION

The invention relates to a compound of the formula

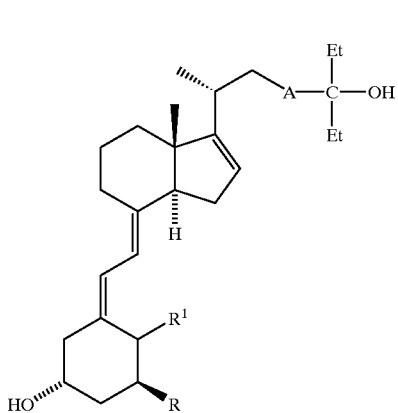

wherein A is

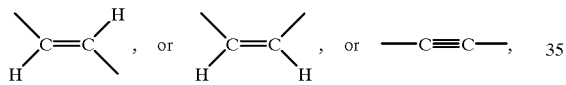

Et is ethyl, and R is hydroxy and $R^1$ is hydrogen or $=CH_2$ or R is hydrogen or fluoro and $R^1$ is $=CH_2$.

Compounds of formula I stimulate HL-60 cell differentiation. Accordingly, the compounds of formula I are useful as agents for the treatment of neoplastic diseases, such as leukemia.

DETAILED DESCRIPTION OF THE INVENTION

As used herein, the term "lower alkyl" denotes a straight or branched-chain alkyl group containing 1 to 4 carbon atoms, for example, methyl, ethyl, propyl, isopropyl, butyl, t-butyl and the like. The term "ar-lower alkyl" are p-tolyl, benzyl, phenylethyl, phenylpropyl, and the like. The term "aryl" denotes a group derived from an aromatic hydrocarbon which may be unsubstituted or substituted by one or more lower alkyl groups. Exemplary of "aryl" are phenyl and p-methyl phenyl.

In the formulas presented herein, the various substituents are illustrated as joined to the nucleus by one of the following notations: a wedged solid line (◄) indicating a substituent which is above the plane of the molecule (β-orientation), and a wedged dotted line (⁞⁞⁞) indicating a substituent which is below the plane of the molecules (α-orientation).

As used herein, the term "E" denotes

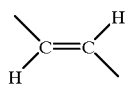

that is, a stereo chemical configuration about a carbon—carbon double bond, such that the two hydrogen are attached to different carbon atoms, and are on opposite sides of the carbon—carbon double bond.

As used herein the term "Z" denotes

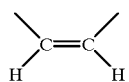

that is, a stereochemical configuration about a carbon—carbon double bond, such that the two hydrogen are attached to different carbon atoms, and are on the same side of the carbon—carbon double bond.

The invention relates to a compound of the formula

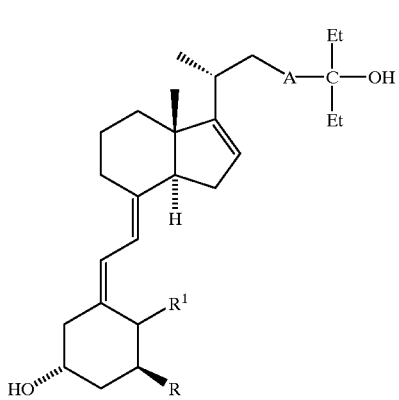

wherein A is

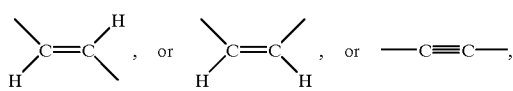

Et is ethyl, and R is hydroxy and $R^1$ is hydrogen or $=CH_2$ or R is hydrogen or fluoro and $R^1$ is $=CH_2$.

Compounds of formula I as described above stimulate differentiation of HL-60 cells. Accordingly, compounds of formula I as described above are useful as agents in the treatment of neoplastic diseases such as leukemia.

The invention relates to a composition comprising a compound of formula I, or a mixture of two or more compounds of formula I.

The invention also relates to a method for treating the above-mentioned disease states by administration of a compound of formula I, or a mixture of two or more compounds of formula I.

The invention also relates to a process for preparing compounds of formula I and the intermediate of formulas II, IX and XIII.

In a preferred embodiment of the compounds of formula I, R is hydroxy and $R^1$ is $=CH_2$. In another compound of formula I, $R^1$ is hydrogen.

Most preferred compounds of formula I are:
1,25-dihydroxy-16-ene-23-yne-26,27-bishomo-cholecalciferol;

1,25-dihydroxy-16,23Z-diene-26,27-bishomo-cholecalciferol;
1,25-dihydroxy-16,23E-diene-26,27-bishomo-cholecalciferol.
The compounds of formula I wherein A is —C≡C— are prepared as hereafter described, with particular reference to formula Scheme I and the Examples below.
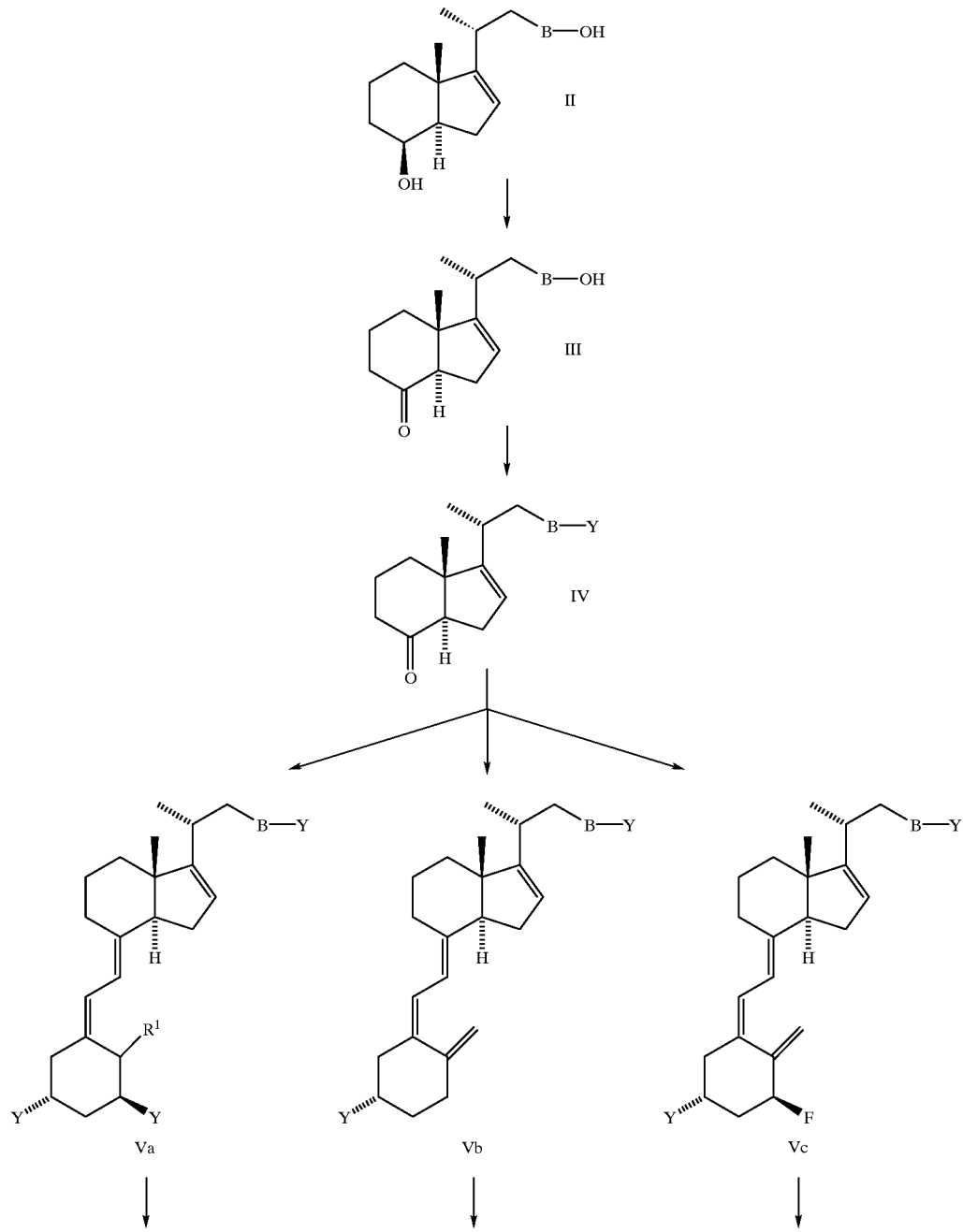

-continued

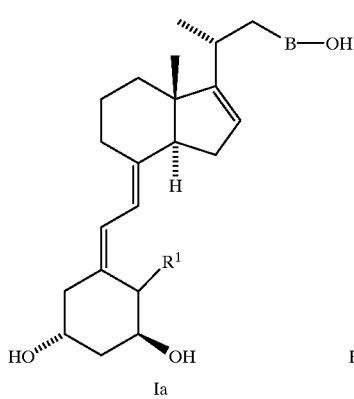
Ia

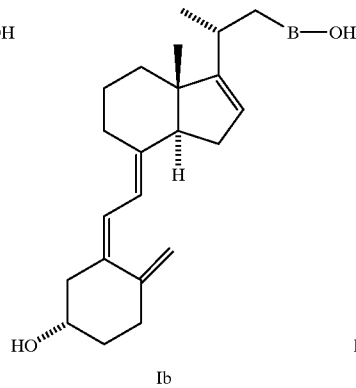
Ib

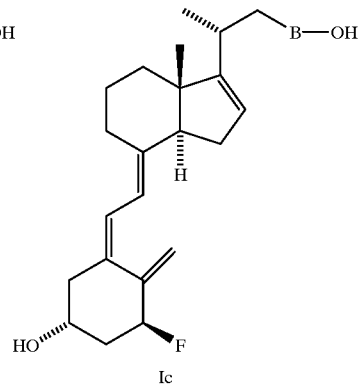
Ic wherein R¹ is as described above, B is

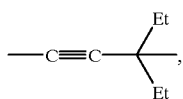

and Y is

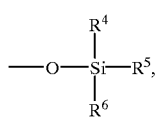

and Et is as described above, $R^4$ and $R^6$ are independently lower alkyl and $R^5$ is independently lower alkyl, aryl or ar-lower-alkyl.

In the above formula Scheme I, the compound of formula II is converted to a compound of formula III by treatment with an oxidizing agent such as 2,2'-bipyridinium chlorochromate or pyridinium dichromate at room temperature, in a aprotic solvent such as dry tetrahydrofuran, or more preferably, dry methylene chloride. The compound of formula III is worked up by conventional means such as extraction followed by chromatography.

The compound of formula III is converted to a compound of formula IV, by reaction with, for example, a (trialkylsilyl) imidazole such as 1-(trimethylsilyl)imidazole in an aprotic, organic solvent such as dry tetrahydrofuran, or more preferably, dry methylene chloride. The compound of formula IV is worked up by conventional means such as extraction followed by chromatography.

The compound of formula IV is converted to a compound of formula Va, Vb or Vc by reaction with the corresponding compound of formula

VI

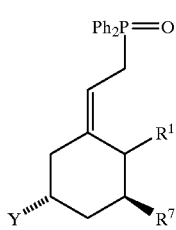

where Ph is phenyl; and Y and R¹ are as described above; $R^7$ is hydrogen, fluorine or Y wherein Y is as described above.

The reaction is carried out at −60° C. to −90° C., preferably −78° C., in a polar, aprotic, organic solvent, such as dry ether or more preferably dry tetrahydrofuran, in the presence of a strong base such as an alkyl lithium like butyl lithium. The compound of formula Va, Vb, or Vc is worked up by conventional means such as extraction followed by chromatography.

Compounds of formula VI are known or can be prepared in accordance with known methods.

The protecting groups of the compound of formula Va, Vb or Vc are removed by reaction with a fluorine salt, such as tetrabutyl-ammonium fluoride in a polar, organic solvent such as dry ether, or more preferably dry tetrahydrofuran to yield a corresponding compound of formula Ia, Ib or Ic.

The intermediate of formula II as described above is prepared as hereinafter described with particular reference to formula Scheme II and the Examples below.

FORMULA SCHEME II

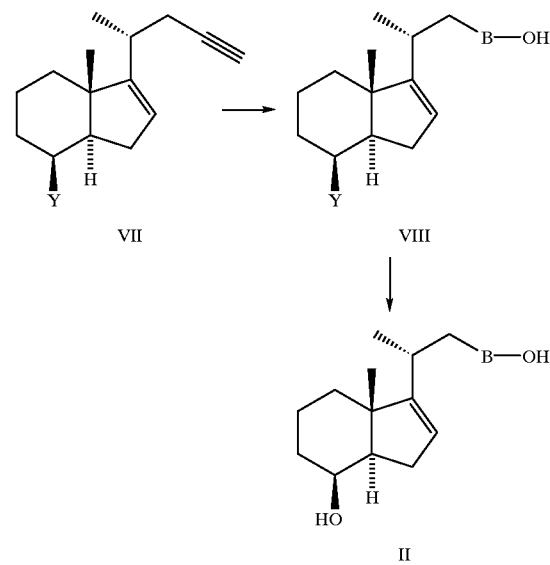

wherein Y and B are as described above.

In the above formula Scheme II, the compound of formula VII is converted to a compound of formula VIII by reaction with 3-pentanone. This reaction is carried out at −60° C. to −90° C., preferably −78° C., in a polar aprotic, organic solvent such as dry ether or more preferably dry tetrahydrofuran, in the presence of a strong base such as an alkyl lithium like butyl lithium. The compound of formula VIII is worked up by conventional means such as extraction followed by chromatography.

The compound of formula VII is known U.S. Pat. No. 5,087,619 and U.S. Pat. No. 5,145,846, both incorporated by reference.

The compound of formula VIII is converted to compound of formula II by reaction with a fluorine salt, such as tetrabutyl-ammonium fluoride in a polar, organic solvent such as dry ether, or more preferably by tetrahydrofuran. The compound of formula II is worked up by conventional means such as extraction followed by chromatography.

The compounds of formula I wherein A is

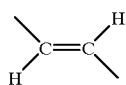

as described above is prepared as hereinafter described with particular reference to formula Scheme III and the Examples below.

FORMULA SCHEME III

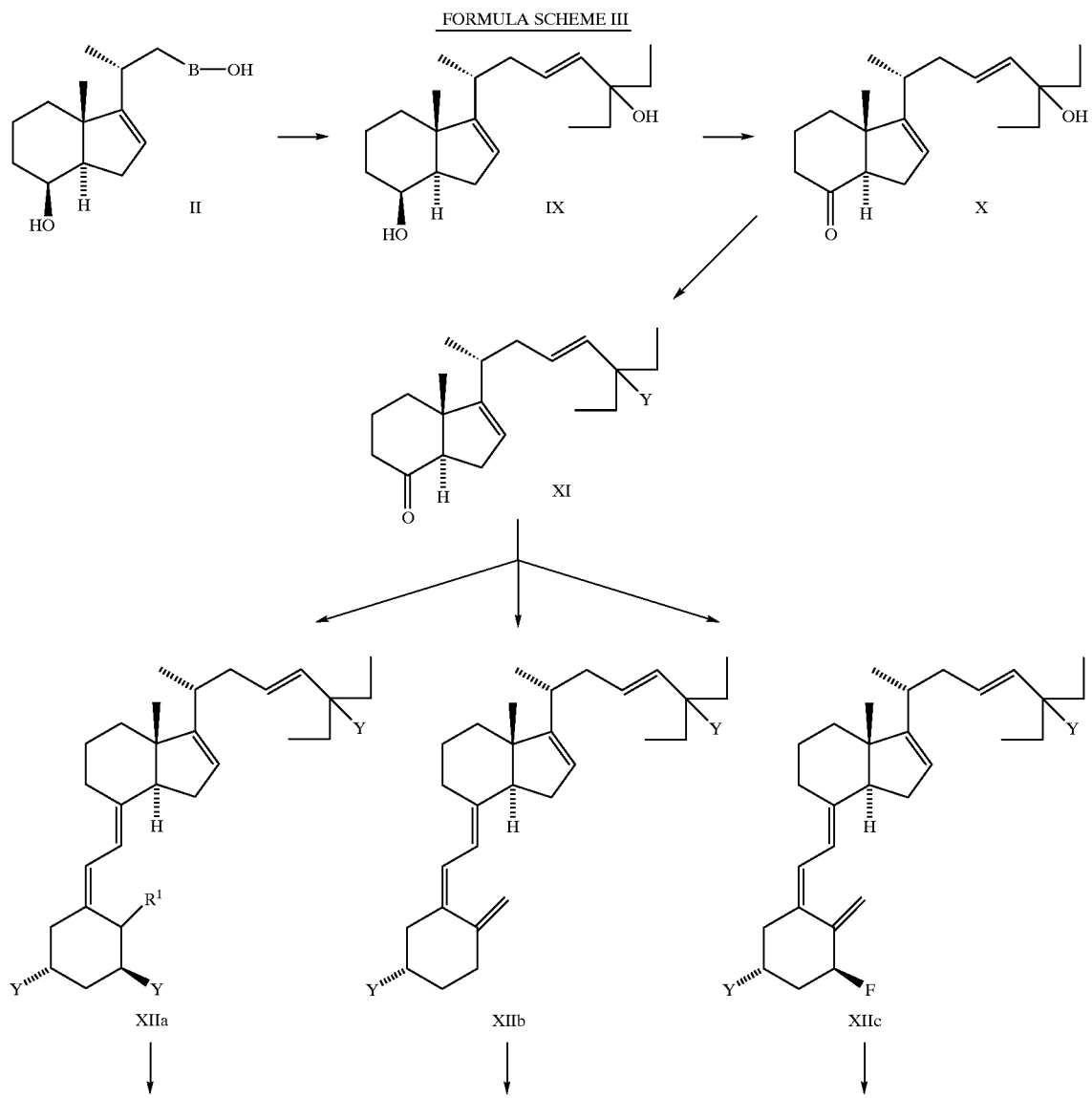

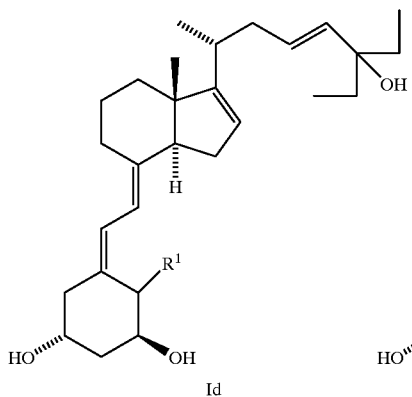
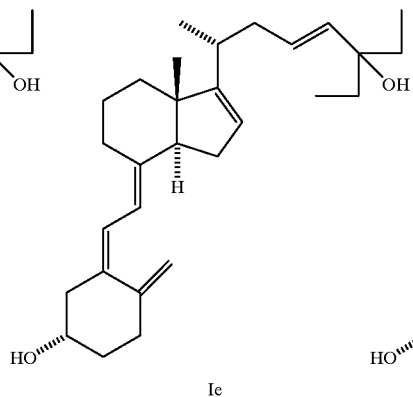
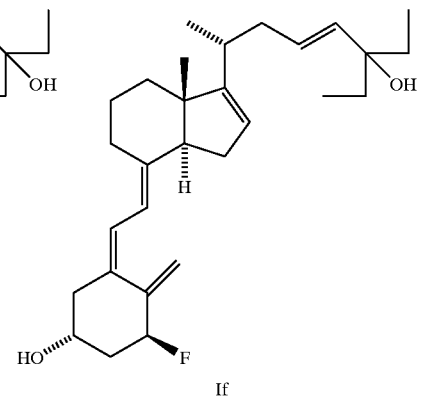

Id                              Ie                              If wherein Y, B and R¹ are as described above.

In the above formula Scheme III, the compound of formula II is partially reduced to obtain a compound of formula IX by reaction with a reducing agent such as lithium aluminum hydride, preferably in the presence of an alkali metal alkoxide, like sodium methoxide, in an aprotic organic solvent like dry ether, or more preferably dry tetrahydrofuran at reflux temperature (about 80° C. for tetrahydrofuran) for about 24 hours, cooled to about 0° C. The compound of formula IX is worked up by conventional means, such as extraction followed by chromatography.

The resulting compound of formula IX is oxidized to the compound of formula X by treatment with an oxidizing agent such as 2,2'-bipyridinium chlorochromate, or pyridinium dichromate, at room temperature, in an aprotic solvent such as dry tetrahydrofuran, or more preferably, dry methylene chloride. The compound of formula X is worked up by conventional means, such as extraction followed by chromatography.

The compound of formula X is converted to a compound of formula XI by reaction with, for example, a (trialkylsilyl) imidazole such as 1-(trimethylsilyl)imidazole in an aprotic, organic solvent such as dry tetrahydrofuran, or more preferably, dry methylene chloride. The compound of formula XI is worked up by conventional means such as extraction followed by chromatography.

The compound of formula XI is converted to a compound of formula XIIa, XIIb, or XIIc by reaction with the corresponding compound of formula VI. The reaction is carried out at −60° C. to −90° C., preferably −78° C., in a polar, aprotic, organic solvent, such as dry ether or more preferably, dry tetrahydrofuran, in the presence of a strong base such as an alkyl lithium like butyl lithium. The compounds of formula XIIa, XIIb, or XIIc is worked up by conventional means such as extraction followed by chromatography.

The protecting groups of the compound of formula XIIa, XIIb, XIIc are removed by reaction with a fluorine salt, such as tetrabutyl ammonium fluoride in an organic solvent such as dry ether, or more preferably by tetrahydrofuran to yield a corresponding compound of formula Id, Ie, or If.

The compounds of formula I wherein A is

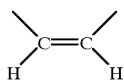

as described above is prepared as hereinafter described with particular reference to formula Scheme IV and the Examples below.

FORMULA SCHEME IV

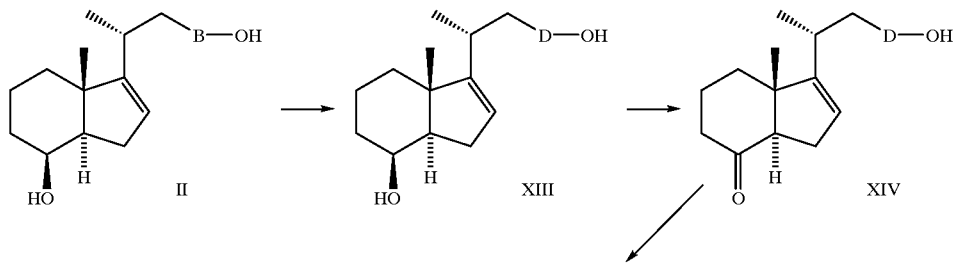

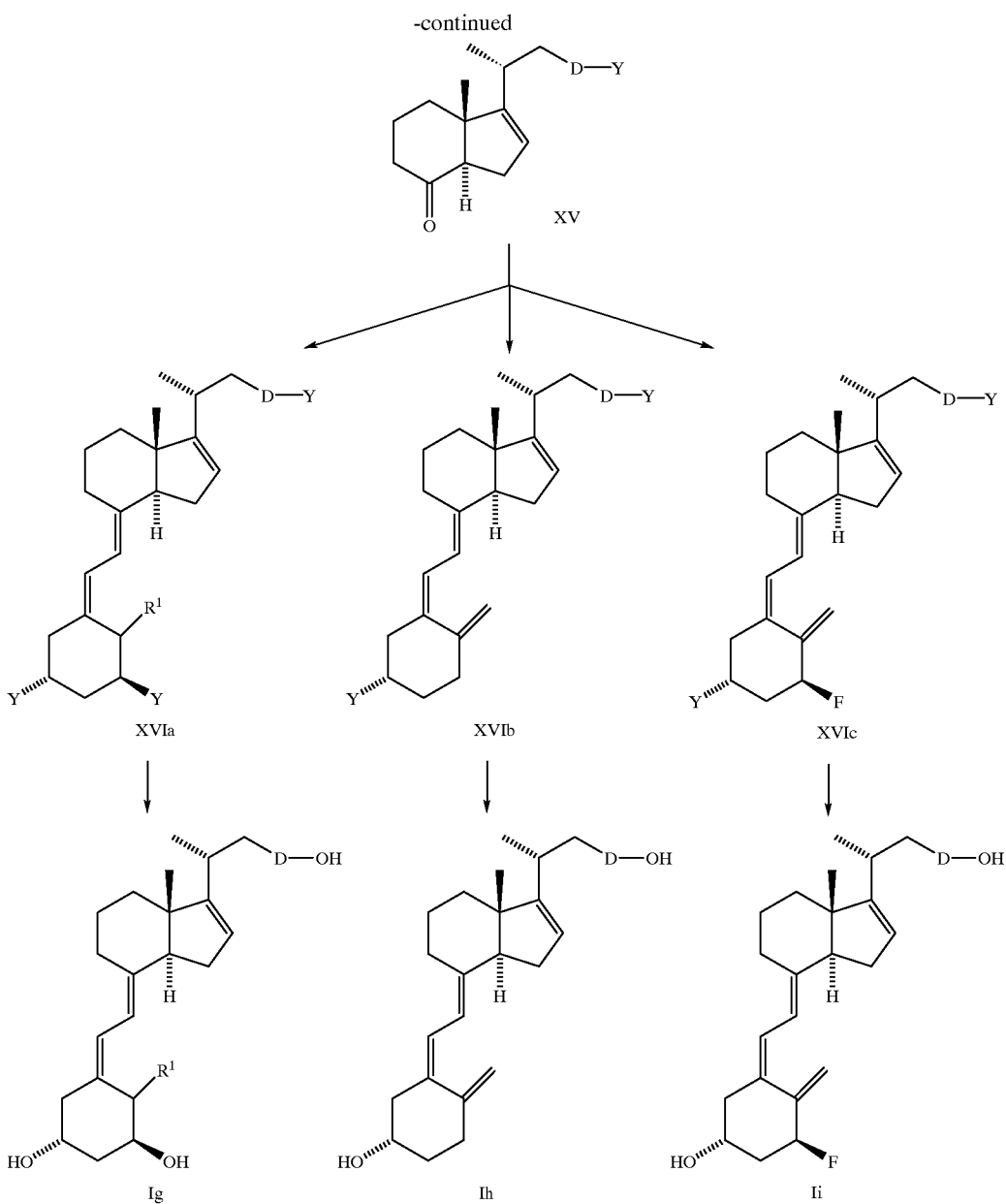

wherein Y, B, and $R^1$ are as described above and D is

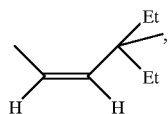

and Et is as described above.

In the above formula Scheme IV, the compound of formula II is hydrogenated to a compound of formula XIII by reaction with hydrogen and a Lindlar catalyst in an organic solvent, such as a combination of ethyl acetate, hexane and ethanol in the presence of quinoline. The compound of formula XIII is worked up by conventional means, such as extraction followed by chromatography.

The resulting compound of formula XIII is oxidized to the compound of formula XIV by treatment with an oxidizing agent such as 2,2'-bipyridinium chlorochromate, or pyridinium dichromate, at room temperature, in an aprotic solvent such as dry tetrahydrofuran, or more preferably, dry methylene chloride. The compound of formula XIV is worked up by conventional means, such as extraction followed by chromatography.

The compound of formula XIV is converted to a compound of formula XV by reaction with, for example, a (trialkylsilyl)imidazole such as 1-(trimethylsilyl)imidazole in an aprotic, organic solvent such as dry tetrahydrofuran, or more preferably, dry methylene chloride.

The compound of formula XV is worked up by conventional means such as extraction followed by chromatography.

The compound of formula XV is converted to a compound of formula XVIa, XVIb, or XVIc by reaction with the corresponding compound of formula VI. The reaction is carried out at −60° C. to −90° C., preferably −78° C., in a polar, aprotic, organic solvent, such as dry ether or more preferably, dry tetrahydrofuran, in the presence of a strong base such as an alkyl lithium like butyl lithium. The compounds of formula XVIa, XVIb, or XVIc is worked up by conventional means such as extraction followed by chromatography.

The protecting groups of the compound of formula XVIIa, XVIIb, XVIIc are removed by reaction with a fluorine salt, such as tetrabutyl ammonium fluoride in an organic solvent such as dry ether, or more preferably by tetrahydrofuran to yield a corresponding compound of formula Ig, Ih, or Ii.

The compounds of formula I as described above can be administered orally, for the treatment of neoplastic diseases such as leukemia, to warmblooded animals which need such treatment. More specifically, the compounds of formula I as described above can be administered orally to an adult human in dosages that are in the range of about 0.05 to 50 µg per day for the treatment of neoplastic diseases such as leukemia.

The useful activity of compounds of formula I as agents for the treatment of neoplastic diseases can be demonstrated by the following test procedures.

HL-60 Cell Differentiation

The induction of differentiation of HL-60 cells was assayed by measuring their oxidative burst potential via the reduction of nitrobluetetrazolium (NBT).

HL-60 cells were maintained in RPMI 1640 medium supplemented with 10% fetal calf serum (FCS), 2 mM L-glutamine, 1 mM sodium pyruvate, 1% non-essential amino acids, 50 U/ml penicillin, and 50 µg/ml streptomycin. HL-60 cells (30,000 cells in 90 µl of supplemented RPMI medium) were seeded into flat-bottomed microliter wells. Immediately after seeding, 10 µl of test compounds listed below in Table I diluted in supplemented RPMI medium were added to the wells to yield final concentrations of between $10^{-11}$ and $10^{-6}$ M (starting from stock solutions of $10^{-2}$ M in ethanol, stored at −20° C. and protected from light). After 3 days, medium was removed from the wells with a multichannel pipette and replaced with 100 µl of NBT solution (1 mg/ml in phosphate buffered saline with 200 nM phorbol myristate acetate). Following an additional hour incubation at 37° C. the NBT solution was removed and 100 µl of 10% sodium dodecyl sulfate in 0.01 N HCl was added. The amount of the reduced NBT was quantified photometrically at 540 nm using an automated plate reader. The mean of 3 wells was calculated. S.E.M. were between 5 and 10%. Values were expressed as percent of maximal differentiation achieved with 100–1000 nM calcitriol in the same experiment. The concentration (nM) leading to 50% of this maximal value is determined graphically and given in Table I as $ED_{50}$.

TABLE I

| COMPOUND | $ED_{50}$ (nM) |
| --- | --- |
| 1,25-Dihydroxy-cholecalciferol | 6.0 |
| 1,25-Dihydroxy-16-ene-23-yne-26,27-bishomo-cholecalciferol | 2.5 |
| 1,25-Dihydroxy-16,23Z-diene-26,27-bishomo-cholecalciferol | 6.2 |
| 1,25-Dihydroxy-16,23E-diene-26,27-bishomo-cholecalciferol | 3.8 |

From the above results, it can be seen that compounds of formula I induce differentiation of HL-60 cells and thereby stop these tumor cells from growing. Accordingly, compounds of formula I are useful in the treatment of neoplastic diseases such as leukemia.

Calcium Tolerance Test In Mice

Profound changes in calcium homeostasis strongly affect the weight development of mice.

Mice (25–30 g body weight) received daily subcutaneous administrations of the compound for 4 consecutive days. Body weight was registered just before and at the end of a 5 day treatment period. The "highest tolerated dose" (HTD) is the dose which results in zero weight gain during this treatment period. The results are set forth in Table II.

TABLE II

| COMPOUND | HTD (µg/kg) |
| --- | --- |
| 1,25-Dihydroxycholecalciferol | 0.5 |
| 1,25-Dihydroxy-16-ene-23-yne-26,27-bishomo-cholecalciferol | 4.0 |
| 1,25-Dihydroxy-16,23Z-diene-26,27-bishomo-cholecalciferol | 2.5 |
| 1,25-Dihydroxy-16,23E-diene-26,27-bishomo-cholecalciferol | 2.0 |

From the above results, it can be seen that the compounds of formula I are better tolerated than 1,25-dihydroxycholecalciferol.

Oral dosage forms comprising compounds of formula I of the invention may be incorporated in capsules, tablets and the like with pharmaceutically acceptable carrier materials.

Illustrative of the pharmaceutically acceptable carrier materials which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

The following Examples are provided to further describe the invention and are not intended to limit it in any way.

EXAMPLE 1

[1(R*),3aR*(3aα,4β,7aβ)]-3a,4,5,6,7,7a-Hexahydro-1-(1-methyl-5-ethyl-5-hydroxy-3-heptynyl)-7a-methyl-4[(trimethylsilyl)oxy]-3H-indene To a solution of 1.02 g (3.51 mmole) of [3aS-[1(R*),3aβ,7β,7aα]-3α,4,5,6,7,7a-hexahydro-3-[1-methyl-3-butynyl]-3a-methyl-7-[(trimethylsilyl)oxy]-1H-indene in 10 ml anhydrous tetrahydrofuran at −78° C. was added slowly 2.5 ml (3.861 mmole) of 1.6M n-butyllithium in hexane. After stirring at −78° C. for one hour, 2.5 ml of 3-pentanone was added and the stirring was continued for additional 15 minutes. The reaction mixture was diluted with water and extracted with 4×50 ml of hexane. The combined extracts were washed with water and brine, dried over sodium sulfate and evaporated to dryness. The crude product was purified by FLASH chromatography to give 273 mg of recovered starting material and 1 g (75%) of the title compound. $^1$H-NMR (CDCl$_3$):δ0.06 (s, 9H, 3CH$_3$), 1.02 (t, 6H, J=7.5 Hz, 2CH$_3$), 1.02 (s, 3H, CH$_3$), 1.10 (d, 3H, J=6Hz CH$_3$), 1.62 (m, 4H, 2CH$_2$), 2.08–2.57 (m, 4H, CH, CH$_2$, CH of CH$_2$), 4.08 (brs, 1H, CH), 5.32 (brs, 1H, CH).

EXAMPLE 2

[1(R*),3a R*(3aα,4β,7aβ)]-3a,4,5,6,7,7a-Hexahydro-1-(1-methyl-5-ethyl-5-hydroxy-3-heptynyl)-7a-methyl-3H-inden-4-ol To a stirred solution of 1.178 g (3.12 mmole) of [1(R*),3aR* (3aα,4β,7aβ)]-3a,4,5,6,7,7a-hexahydro-1-[1-methyl- 5-ethyl-5-hydroxy-3-heptynyl)-7a-methyl-4-[(trimethylsilyl)oxy]-3H-indene in 15 ml anhydrous tetrahydrofuran was added 6 ml (6 mmole) of 1M tetrabutyl ammonium fluoride. The reaction mixture was stirred at room temperature overnight in an argon atmosphere. It was then diluted with 150 ml of water-brine 1:1 and extracted thoroughly with ethyl acetate. The combined extracts were washed with 2×30 ml water, dried over sodium sulfate and evaporated to dryness. The crude product was purified by FLASH chromatography to give 900 mg (94.5%) of the title compound, as a white crystalline solid.

$[\alpha]_D^{25}$ −20.5° (c 0.2, EtOH); $^1$H-NMR (CDCl$_3$);δ1.01 (t, 6H, J=7.3 Hz, 2CH$_3$), 1.07 (s, 3H, CH$_3$), 1.10 (d,3H,J=6 Hz, CH$_3$), 140(dt,1H,Jvic=3.5 and 12.5 Hz, Jgem=12.5 Hz, CH of CH$_2$), 1.63 (m, 4H, 2 CH$_2$), 1.98 (ddd, 1H, Jvic=3.5 and 5.5 Hz, Jgem=15 Hz, CH of CH$_2$), 2.20–2.45 (m, 4H, CH$_2$, 2CH of CH$_2$), 4.19 (brs, 1H, CH), 5.39 (s, 1H, CH). Analysis Calcd. for C$_{20}$H$_{32}$O$_2$: C 78.90, H 10.59. Found: C 78.92, H 10.30.

EXAMPLE 3

[1(R*),3aR*(3aα,7aβ)]-3,3a,5,6,7,7a-Hexahydro-1-(1-methyl-5-ethyl-5-hydroxy-3-heptynyl)-7a-methyl-4H-inden-4-one To a stirred solution of 253 mg (0.83 mmole) of [1(R*), 3aR* (3aα,4β,7aβ)]-3a,4,5,6,7,7a-hexahydro-1(1-methyl-5-ethyl-5-hydroxy-3-heptynyl)-7a-methyl-3H-inden-4-ol in 15 ml anhydrous methylene chloride at room temperature in argon atmosphere was added 1 g of (2.65 mmole) of pyridinium dichromate. The reaction mixture was stirred for two hours, 0.5 g of 3A molecular sieves was added, and the stirring was continued for one hour. After addition of 25 ml of ether and stirring for 15 minutes, it was filtered through a celite pad. The pad was washed with 3×50 ml ethyl acetate. The combined filtrates were washed with 2N potassium bicarbonate, water and brine, dried over sodium sulfate and evaporated to dryness. The crude product was purified by FLASH chromatography to give 157 mg (62%) of the title compound.

EXAMPLE 4

[1(R*),3aR*(3aα,7aβ)]-3,3a,5,6,7,7a-Hexahydro-1-(1-methyl-5-ethyl-5-[(trimethylsilyl)oxy]-3-heptynyl)-7a-methyl-4H-inden-4-one To a solution of 223 mg (0.737 mmole) of [1(R*),3aR*-(3aα,7aβ)]-3,3a,4,5,6,7,7a-hexahydro-1( 1-methyl-5-ethyl-5-hydroxy-3-heptynyl)-7a-methyl-4H-inden-4-one in 10 ml anhydrous methylene chloride was added 0.67 ml (4.42 mmole) of 1-(trimethylsilyl)-imidazole. The reaction mixture was stirred at room temperature in an argon atmosphere overnight. The reaction was quenched with water, and extracted with hexane. The hexane extracts were washed with water and brine dried over sodium sulfate and evaporated to dryness. The crude product was purified by FLASH chromatography with hexane-ethyl acetate 10:1 to give 272 mg (98%) of the title compound. $^1$H-NMR (CDCl$_3$): δ0.15 (s, 9H, 3CH$_3$), 0.83 (s, 3H, CH$_3$), 0.91 (t, 6H, J=7.5 Hz, 2CH$_3$), 1.16 (m, 3H, CH$_3$), 1.57 (q, 4H, J=7.5, 2CH$_2$), 2.85 (dd, 1H, Jvic=7 Hz, Jgem=10 Hz, CH of CH$_2$), 5.37 (brs, 1H, CH).

EXAMPLE 5

1,25-Dihydroxy-16-ene-23-yne-26,27-bishomo-cholecalciferol

To a stirred solution of 694 mg (1.19 mmole) of [3S-(1Z, 3α,5β)-[2-[3,5-bis[[1,1-dimethylethyl)dimethylsilyl]oxy]-2-methylene-cyclohexylidene]ethyl]diphenylphosphine oxide in 10 ml anhydrous tetrahydrofuran at −78° C. was added 0.75 ml (1.2 mmole) of 1.6 M n-butyllithium in hexane. The reaction mixture turned red immediately and the color persisted during the addition of 270 mg (0.72 mmole) of [1(R*),3aR*(3aα,7aβ)]-3,3a,5,6,7,7a-hexahydro-1-(1-methyl-5-ethyl-5-[(trimethylsilyl)oxy]-3-heptynyl)-7a-methyl-4H-inden-4-one in 8 ml of anhydrous tetrahydrofuran. The reaction mixture was stirred at −78° C. for 90 min, and then quenched with brine and extracted with ethyl acetate. The combined extracts were washed with water and brine, dried over sodium sulfate and evaporated to dryness. The crude intermediate was purified by FLASH chromatography with hexane-ethyl acetate 40:1 to give 498 mg of trisilylated intermediate.

To the solution of trisilylated intermediate (498 mg) in 10 mg anhydrous tetrahydrofuran was added 5.04 ml (5.04 mmole) of a 1M tetrabutyl ammonium fluoride. The reaction mixture was stirred at room temperature under argon for 48 hours, and then diluted with water and extracted with ethyl acetate. The combined extracts were washed with water and brine, over sodium sulfate and evaporated to dryness. The crude product was purified by FLASH chromatography with hexane-ethyl acetate 1:3 and preparative HPLC with hexane-ethyl acetate 1:4 to give 267 mg (84.5%) of the title compound, $[\alpha]_D^{25}$+6° (c 0.2, EtOH); UV λ max:262/3 nm (ε19,100); 1H-NMR (CDCl$_3$): δ0.72 (s, 3H, CH$_3$), 1.01 (t,6H,J=6.8 Hz, 2 CH$_3$), 1.14 (d,3H,J=6.2 Hz, CH$_3$), 1.62 (m,4H, 2CH$_2$), 1.92 (ddd, 1H, Jvic=3.5 and 8.5 Hz, Jgem= 12.5 Hz, CH of CH$_2$), 2.61 (br dd, 1H, Jvic=3.5 Hz, Jgem=12.5 Hz, CH of CH$_2$), 2.82 (dd, 1H, Jvic=4 Hz, Jgem=12 Hz, CH of CH$_2$), 4.24 (brm, 1H, CH), 4.45 (brm, 1H, CH), 5.02, 5.34 (2s, 2H, CH$_2$), 5.38 (s, 1H, CH), 6.11, 6.38 (AB;2H, J=11.4 Hz, CH CH).

EXAMPLE 6

[1(R*),3aR*(3aα,4β,7aβ)]-3a,5,6,7,7a-Hexahydro-1-(1-methyl-5-ethyl-5-hydroxy-3E-heptenyl)-7a-methyl-3H-inden-4-ol To a stirred suspension of 190 mg (5 mmole) of lithium aluminum hydride in 15 ml anhydrous tetrahydrofuran cooled in an ice-bath was added carefully 270 mg (5 mmole) of solid sodium methoxide first, followed by addition of 252 mg (0.852 mmole) of [1(R*),3aR*-(3aα,4β,7aβ)]-3a,4,5,6, 7,7a-hexahydro-1(1-methyl-5-ethyl-5-hydroxy-3-heptynyl)-7a-methyl-3H-inden-4-ol and the reaction mixture was heated at reflux for 24 hours. After cooling in ice-bath, the reaction was quenched by careful addition of 1 ml water, followed by addition of 1 ml of 2N NaOH. After addition of 20 ml ether, it was stirred for 0.5 hr; 2.2 g Mg SO$_4$ was added and stirred for another 0.5 hr. It was then filtered, filter washed with ether, and the combined ether filtrates were evaporated to dryness. The crude product was purified by FLASH chromatography and preparative HPLC with hexane-ethyl acetate 2:1 to give 133 mg (53%) of the title compound. $^1$H-NMR (CDCl$_3$): δ0.84 (t, 6H, J=7.5 Hz, 2CH$_3$), 0.99 (d, 3H, J=6 Hz, CH$_3$), 1.03 (s, 3H, CH$_3$), 1.51 (q, 4H, J=7.5 Hz, 2CH$_2$), 4.17 (brs, 1H, CH), 5.32 (brs, 1H, CH), 5.38 (d, 1H, Jtrans=16.5 Hz, CH), 5.52 (dt, 1H, Jvic=6.5 Hz, Jtrans=16.5 Hz, CH).

EXAMPLE 7

[1(R*),3aR*(3aα,7aβ)]-3,3a,5,6,7,7a-Hexahydro-1-(1-methyl-5-ethyl-5-hydroxy-3E-heptenyl)-7a-methyl-4H-inden-4-one To a stirred of 133 mg (0.434 mmole) of [1(R*),3aR* (3aα,4β,7aβ)]-3a,4,5,6,7,7a-hexahydro-1(1-methyl-5-ethyl- 5-hydroxy-3E-heptenyl)-7a-methyl-3H-inden-4-ol in 4 ml anhydrous methylene chloride was added 950 mg (2.527 mmole) of pyridinium dichromate at room temperature in an argon atmosphere. The reaction mixture was stirred for 5 hours. Then, 25 ml of ether was added and stirred for 15 minutes, filtered through celite pad, and the pad was washed with 3×40 ml of ethyl acetate. The combined filtrates were evaporated to dryness. The crude product was purified by FLASH chromatography with hexane-ethyl acetate 5:2 to give 111 mg (84%) of the title compound.

EXAMPLE 8

[1(R*),3aR*(3aα,7aβ)]-3,3a,5,6,7,7a-Hexahydro-1-(1-methyl-5-ethyl-5-[(trimethylsilyl)oxy]-3E-heptenyl)-7a-methyl-4H-inden-4-one To a solution of 111 mg (0.365 mmole) of [1(R*),3aR*-(3aα,7aβ)]-3,3a,5,6,7,7a-hexahydro-1-(1-methyl-5-ethyl-5-hydroxy-3E-heptenyl)-7a-methyl-4H-inden-4-one in 4 ml anhydrous methylene chloride was added 0.375 ml (2.56 mmole) of 1-(trimethylsilyl)-imidazole. The reaction mixture was stirred in an argon atmosphere for 23 hours. It was then quenched by addition of 10 ml water, stirring for 15 minutes, addition of 20 ml of brine and extraction with 3×90 ml of ethyl acetate. The organic layers were washed five times with water-brine 1:1, dried over sodium sulfate and evaporated to dryness. The crude product was purified by FLASH chromatography with hexane-ethyl acetate 10:1 to give 131 mg (95%) of the title compound.

EXAMPLE 9

1,25-Dihydroxy-16,23E-diene-26,27-bishomo-cholecalciferol

To a stirred solution of 405 mg (0.695 mmole) of [3S-(1Z,3α,5β)]-[2-[3,5-bis[[1,1-dimethylethyl)dimethylsilyl]oxy]- 2-methylene-cyclohexylidene]ethyl] diphenylphosphine oxide in 5 ml anhydrous tetrahydrofuran at −78° C. was added 0.434 ml (0.694 mmole) of 1.6 M n-butyllithium in hexane dropwise in an argon atmosphere. After 5 minutes of stirring, to the thus obtained red solution was added dropwise over a 10 minute period a solution of 131 mg (0.348 mmole) of [1(R*),3aR*(3aα,7aβ)]-3,3a,5,6,7,7a-hexahydro-1-(1-methyl-5-ethyl-5-[(trimethylsilyl)oxy]-3E-heptenyl)-7a-methyl-4H-inden-4-one in 4 ml of anhydrous tetrahydrofuran. The reaction mixture was then stirred at −78° C. for 2 hours. It was quenched by addition of 10 ml 2N Rochelle salt solution and warming up to room temperature, then extracted with 3×90 ml of ethyl acetate. The combined extracts were washed three times with brine, dried over sodium sulfate and evaporated to dryness. The residue was purified by FLASH chromatography with hexane-ethyl acetate 30:1 to give 220 mg of the trisilylated intermediate.

To the solution of trisilylated intermediate (220 mg) in 3 ml anhydrous tetrahydrofuran was added 3.2 ml (3.2 mmole) of 1M tetrabutyl ammonium fluoride in tetrahydrofuran, and this reaction mixture was stirred at room temperature in an argon atmosphere for 19 hours. 5 ml of Water was then added, stirred for 15 minutes, diluted with 20 ml brine and extracted with 3×90 ml ethyl acetate. The combined extracts were washed with water-brine 1:1, dried over sodium sulfate and evaporated to dryness. The crude product was purified by FLASH chromatography and by preparative HPLC with hexane-ethyl acetate 1:5 to give 126 mg (82%) of crystalline title compound; m.p. 133–135° C. (from 4:6 tetrahydrofuran-methyl formate). $[\alpha]_D^{25}$+26° (c0.2, EtOH); UV λ max (EtOH): 263 nm (ε 18,200); $^1$H-NMR (CDCl$_3$): δ0.69 (s, 3H,CH$_3$), 0.85 (t, 6H, J=7.5 Hz, 2CH$_3$), 1.02 (d,3H, J=6,7 Hz, CH$_3$), 1.52 (m, 4H, 2CH$_2$), 1.68 (m, 1H CH of CH$_2$), 1.91 (ddd, 1H, Jvic=3.5 and 8.5 Hz, Jgem=12.5 Hz, CH of CH$_2$), 2.60 (dd, 1H, Jvic=3.5 Hz, Jgem=12.5 Hz, CH of CH$_2$), 2.82 (m, 1H, CH of CH$_2$), 4.24 (m, 1H, CH), 4.45 (m, 1H, CH), 5.02, 5.34 (2s, 2H, CH$_2$), 5.32 (brs, 1H, CH), 5.38 (d, 1H, Jtrans=15.5 Hz, CH), 5.52 (dt, 1H, Jvic=7Hz, Jtrans=15.5 Hz, CH), 6.11, 6.38 (AB, 2H, J=11.5 Hz, CH CH); Analysis: Calcd for C$_{29}$H$_{44}$O$_3$:C 79.04, H 10.06; Found: C 78.78, H 10.21.

EXAMPLE 10

[1(R*),3aR*-(3aα,4β,7aβ)]-3a,4,5,6,7,7a-Hexahydro-1-(1-methyl-5-ethyl-5-hydroxy-3Z-heptenyl)-7a-methyl-3H-inden-4-ol A mixture of 215 mg (0.71 mmole) of [1(R*),3aR*-(3aα,4β,7aβ)]-3a,4,5,6,7,7a-hexahydro-1-(1-methyl-5-ethyl-5-hydroxy-3-heptenyl)-7a-methyl-3-inden-4-ol, 5 ml ethyl acetate, 12.5 ml hexane, 0.35 ml absolute ethanol, 0.0175 ml quinoline and 35 mg of Lindlar catalyst was hydrogenated at room temperature and normal pressure for 1.5 hours. The reaction mixture was filtered through a Celite pad, and the pad was washed with ethyl acetate. The combined filtrates were washed with 1N HCl, water, 2N potassium bicarbonate, water and brine, dried over sodium sulfate and evaporated to dryness. The crude product was purified by preparative HPLC (YMC column) to give 200 mg (92.5% of the title compound). $^1$H-NMR (CDCl$_3$): δ0.90 (t,6H,J=7.5 Hz, 2CH$_3$, 1.01 (d,3H, J=6.5 Hz, CH$_3$), 1.05 (s, 3H, CH$_3$), 1.57(q, 4H, J=7.5 Hz, 2CH$_2$), 4.17 (brs, 1H, CH), 5.22 (br dt, 1H, Jvic=1.5 Hz, Jcis=12 Hz, CH), 5.38 (dt, 1H, Jvic=7 Hz, Jcis=12 Hz, CH).

EXAMPLE 11

[1(R*),3aR*-(3aα,7aβ)]-3,3a,5,6,7,7a-Hexahydro-1-(1-methyl-5-ethyl-5-hydroxy-3Z-heptenyl)-7a-methyl-4H-inden-4-one To a stirred solution of 200 mg (0.652 mmole) of [1(R*),3aR*-(3aα,4β,7aβ)]-3a,4,5,6,7,7a-hexahydro-1-(1-methyl-5-ethyl-5-hydroxy-3Z-heptenyl)-7a-methyl-3H-inden-4-ol in 10 ml anhydrous methylene chloride was added 1.286 g (3.301 mmole) of pyridinium dichromate at room temperature in an argon atmosphere. The reaction mixture was stirred for 6 hours. 25 ml of Ether was added and stirred for 15 minutes, filtered through a Celite pad, and the pad was washed with 3×25 ml ethyl acetate. The combined filtrates were evaporated to dryness. The crude product was purified by FLASH chromatography with hexane-ethyl acetate 3:1, to give 182 mg (91.5%) of the title compound. $^1$H-NMR (CDCl$_3$): 0.81 (s, 3H, CH$_3$), 0.88 (t, 6H, J=7.5 Hz, 2CH$_3$), 1.06 (d, 3H, J=6.5 Hz, CH$_3$), 1.56 (q, 4H, J=7.5 Hz, 2CH$_2$), 2.84 (dd, 1H, Jvic=6.5 Hz, Jgem=10 Hz, CH of CH$_2$), 5.22 (d, 1H, Jcis=12 Hz, CH), 5.33 (s, 1H, CH), 5.35 (dt, 1H, Jvic=6.5 Hz, Jcis=12 Hz, CH).

EXAMPLE 12

[1(R*),3aR*-(3aα,7aβ)]-3,3a,5,6,7,7a-Hexahydro-1-(1-methyl-5-ethyl-5-[(trimethylsilyl)oxy-3Z-heptenyl)-7a-methyl-4H-inden-4-one To a solution of 182 mg (0.597 mmole) of [1(R*),3aR*-(3aα,7aβ)]-3,3a,5,6,7,7a-hexahydro-1-(1-methyl-5-ethyl-5-hydroxy-3Z-heptenyl)-7a-methyl-4H-inden-4-one in 10 ml anhydrous methylene chloride was added 0.542 ml (3.58 mmole) of 1-(trimethylsilyl)-imidazole. The reaction mixture was stirred at room temperature overnight. The reaction mixture was then diluted with hexane, washed with water and brine, dried over sodium sulfate and evaporated to dryness. The crude product was purified by FLASH chromatography with hexane-ethyl acetate 10:1 to give 218 mg (97%) of the title compound. $^1$H-NMR (CDCl$_3$): δ0.12 (s, 9H, 3CH$_3$), 0.80 (s, 3H, CH$_3$), 0.86(t, 6H, J=7.5 Hz, 2CH$_3$), 1.05 (d, 3H, J=6.5 Hz, CH$_3$), 1.55 (q, 4H, J=7.5 Hz, 2CH$_2$), 2.84 (dd, 1H, Jvic=6.5 Hz, Jgem=10 Hz, CH of CH$_2$), 5.08 (br dt, 1H, Jvic=1.5 Hz, Jcis=11.5 Hz, CH), 5.25 (dt, 1H, Jvic=6.5 Hz, Jcis=11.5 Hz, CH), 5.31 (brs, 1H, CH).

EXAMPLE 13

1,25-Dihydroxy-16,23Z-diene-26,27-bishomo-cholecalciferol

To a stirred solution of 578 mg (0.992 mmole) of [3S-(1Z,3α,5β)]-[2-[3,5-bis[[(1,1-dimethylethyl)dimethylsilyl]oxy]-2-methylene-cyclohexylidene]ethyl]diphenylphosphine oxide in 8 ml of anhydrous tetrahydrofuran at −78° C. was added 0.62 ml (0.992 mmole) of 1.6M n-butyllithium in hexane dropwise in an argon atmosphere. The reaction mixture turned red and the color persisted during the addition of 218 mg (0.578 mmole) of [1(R*),3aR*(3aα,7aβ)]-3,3a,5,6,7,7a-hexahydro-1-(1-methyl-5-ethyl-5[(trimethylsilyl)oxy]-3Z-heptenyl)-7a-methyl-4H-inden-4-one in 8 ml anhydrous tetrahydrofuran. The reaction mixture was stirred at −78° C. for 2 hours, then quenched with water and extracted thoroughly with ethyl acetate. The combined extracts were washed with water and brine, dried over sodium sulfate and evaporated to dryness. The crude intermediate was purified by FLASH chromatography with hexane-ethyl acetate 20:1 to give 328 mg of the trisilylated intermediate.

To the solution of the trisilylated intermediate (328 mg) in 10 ml anhydrous tetrahydrofuran was added 4 ml (4 mmole) of 1M tetrabutyl ammonium fluoride in tetrahydrofuran, and the reaction mixture was stirred at room temperature overnight. It was then diluted with water and extracted with ethyl acetate. The combined extracts were washed with water and brine, dried over sodium sulfate and evaporated to dryness. The crude product was purified by preparative HPLC (YMC column) with hexane-ethyl acetate 1:4 to give 191 mg (75%) of the title compound as white foam. [α]$_D^{25}$+20.5° (c 0.2, EtOH); UVλ (EtOH): 262–263 nm (ε=14450); $^1$H-NMR (CDCl$_3$); δ0.7 (s, 3H, CH$_3$), 0.9 (t,6H, J=7.3 Hz, 2 CH$_3$), 1.05 (d, 3H, J=6.8 Hz, CH$_3$), 1.57 (m, 4H, 2CH$_2$), 1.91 (ddd, 1H, Jvic=3.5 and 8.5 Hz, Jgem=12.5 Hz, CH of CH$_2$), 2.48 (m, 2H, CH$_2$), 2.61 (br d, 1H, Jgem=12.5 Hz, CH of CH$_2$), 2.82 (br m, 1H, CH of CH$_2$), 4.24 (br m, 1 H, CH), 4.45 (br m, 1H, CH), 5.02, 5.34 (2s, 2H, CH$_2$), 5.23 (d, 1H, Jcis=12.3 Hz, CH), 5.35 (s, 1H, CH), 5.37 (dt, 1H, Jvic=7 Hz, Jcis=12.3 Hz, CH), 6.11, 6.38 (AB, 2H, J=11.3 Hz, CH CH).

Oral Dosage Form Soft Gelatin Capsule

| | mg/capsule |
|---|---|
| 1,25-dihydroxy-16,23E-diene-26,27-bishomo-cholecalciferol (Compound A) | 0.0005–0.050 |
| Butylated Hydroxytoluene (BHT) | 0.016 |
| Butylated Hydroxyanisole (BHA) | 0.016 |
| Myglyol ®-812 qs | 160 |

1. Suspend BHT and BHA in Myglyol®-812. Warm to about 50° C., and stir until dissolved.
2. Dissolve Compound A in the solution from Step 1.
3. Fill the solution from Step 2 in a soft gelatin cap.

All steps are performed under a nitrogen atmosphere and protected from light.

Oral Dosage Form Soft Gelatin Capsule

| | mg/capsule |
|---|---|
| Compound A | 0.0005–0.050 |
| α-Tocopherol | 0.016 |
| Myglyol ®-812 qs | 160 |

1. Suspend α-Tocopherol in Myglyol®-812. Warm to about 50° C., and stir until dissolved.
2. Dissolve Compound A in the solution from Step 1.
3. Fill the solution from Step 2 in a soft gelatin cap.

All steps are performed under a nitrogen atmosphere and protected from light.

What is claimed is:

1. A compound of the formula

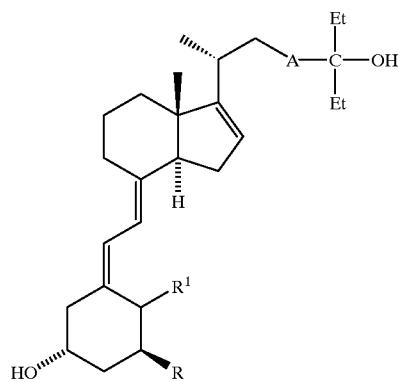

I wherein A is

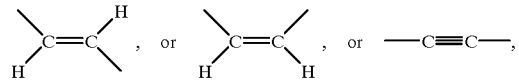

Et is ethyl, and R is hydroxy and R$^1$ is hydrogen or =CH$_2$ or R is hydrogen or fluoro and R$^1$ is =CH$_2$.

2. A compound in accordance with claim 1, wherein A is

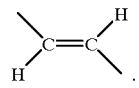

3. A compound in accordance with claim 2, wherein R is hydroxy.
4. A compound in accordance with claim 2, wherein R$^1$ is =CH$_2$.
5. A compound in accordance with claim 2, 1,25-dihydroxy-16,23E-diene-26,27-bishomo-cholecalciferol.
6. A compound in accordance with claim 1, wherein A is

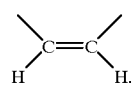

7. A compound in accordance with claim 6, wherein R is hydroxy.

8. A compound in accordance with claim 6, wherein $R^1$ is $=CH_2$.

9. A compound in accordance with claim 6, 1,25-dihydroxy-16,23Z-diene-26,27-bishomo-cholecalciferol.

10. A compound in accordance with claim 1, wherein A is

11. A compound in accordance with claim 10, wherein R is hydroxy.

12. A compound in accordance with claim 10, wherein $R^1$ is $=CH_2$.

13. A compound in accordance with claim 10, 1,25-dihydroxy-16-ene-23-yne-26,27-bishomo-cholecalciferol.

14. A compound in accordance with claim 1, 1α-fluoro-25-hydroxy-16,23E-diene-26,27-bishomo-cholecalciferol.

15. A pharmaceutical composition comprising (a) an effective amount of a compound of the formula

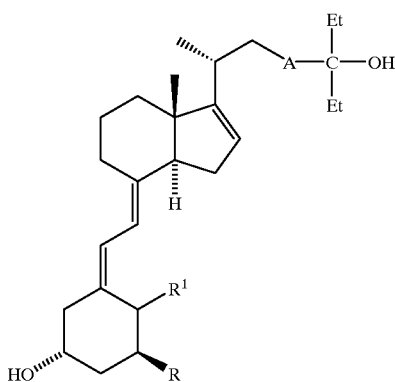

I wherein A is

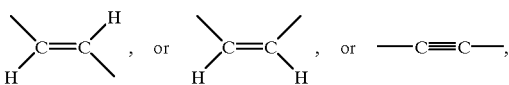

Et is ethyl, and R is hydroxy and $R^1$ is hydrogen or $=CH_2$ or R is hydrogen or fluoro and $R^1$ is $=CH_2$ and (b) an inert carrier.

16. A pharmaceutical composition in accordance with claim 15, wherein A is

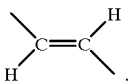

17. A pharmaceutical composition in accordance with claim 16, wherein the compound of formula I is 1,25-dihydroxy-16,23E-diene-26,27-bishomo-cholecalciferol.

18. A pharmaceutical composition in accordance with claim 15, wherein A is

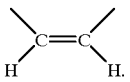

19. A pharmaceutical composition in accordance with claim 18, wherein the compound of formula I is 1,25-dihydroxy-16,23Z-diene-26,27-bishomo-cholecalciferol.

20. A pharmaceutical composition in accordance with claim 15, wherein A is

21. A pharmaceutical composition in accordance with claim 20, wherein the compound of formula I is 1,25-dihydroxy-16-ene-23-yne-26,27-bishomo-cholecalciferol.

22. The pharmaceutical composition in accordance with claim 15, wherein the compound of formula I is 1α-fluoro-25-hydroxy-16,23E-diene-26,27-bishomo-cholecalciferol.

* * * * *